United States Patent [19]

Solorzano

[11] Patent Number: 4,642,128
[45] Date of Patent: Feb. 10, 1987

[54] SMOKE EVACUATOR SYSTEM WITH ELECTRONIC CONTROL CIRCUITRY

[75] Inventor: Armando N. Solorzano, Colorado Springs, Colo.

[73] Assignee: Xanar, Inc., Colorado Springs, Colo.

[21] Appl. No.: 774,693

[22] Filed: Sep. 11, 1985

[51] Int. Cl.⁴ .................. B01D 35/14; B01D 46/42
[52] U.S. Cl. .............................. 55/217; 55/274; 55/467; 55/DIG. 34; 340/607
[58] Field of Search ............ 55/217, 274, 467, 470, 55/DIG. 34, 267, 276, 419; 340/607, 584, 528, 527

[56] References Cited

U.S. PATENT DOCUMENTS

| | | | |
|---|---|---|---|
| 2,625,239 | 1/1953 | Senne | 55/217 |
| 2,715,452 | 8/1955 | Kent | 55/217 |
| 3,046,718 | 7/1962 | Ide et al. | 55/470 X |
| 3,232,030 | 2/1966 | Owenmark | 55/217 |
| 3,477,087 | 11/1969 | Robinson | 55/467 X |
| 3,510,904 | 5/1970 | Lagerstrom | 55/217 X |
| 3,812,370 | 5/1974 | LaViolette | 55/274 X |
| 4,121,199 | 10/1978 | Young | 55/274 X |
| 4,129,426 | 12/1978 | Furasen | 55/217 |
| 4,253,852 | 3/1981 | Adams | 55/150 X |

Primary Examiner—Kathleen J. Prunner
Attorney, Agent, or Firm—Donal B. Tobin

[57] ABSTRACT

A laser surgery smoke evacuator system is disposed within a small, thermally and acoustically insulated casing. The system includes a filter, a vacuum pump disposed downstream of the filter, an alternating current motor driven by an AC power source, a DC power supply energized by the AC source, an AC phase controller to vary the motor speed, a capacitor circuit to isolate the phase control from electromotive interference and a filter clog circuit. The DC power supply powers the phase controller and the capacitor and filter clog circuits. The AC phase controller is mounted next to an air intake in the casing for cooling the motor. The motor drives the vacuum pump which evacuates smoke from a laser surgery site, draws such smoke through the filter and exhausts clean air from the casing. A temperature controller disposed between the filter and pump is connected to the filter clog circuit, monitors the clogged condition of the filter and energizes an indicator on the casing to notify the user of the clogged condition of the filter.

3 Claims, 4 Drawing Figures

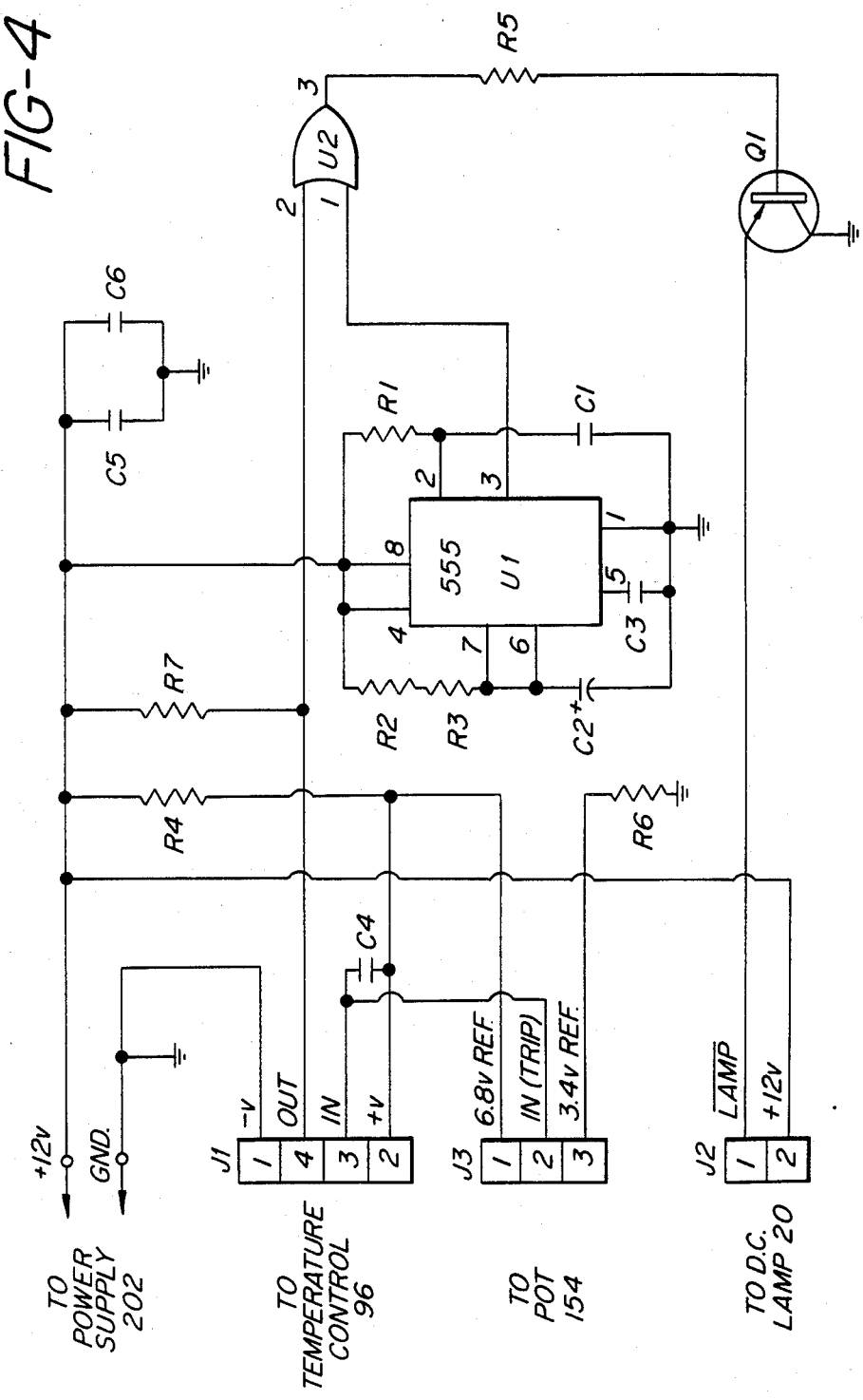

SMOKE EVACUATOR SYSTEM WITH ELECTRONIC CONTROL CIRCUITRY

FIELD OF THE SYSTEM

An electronic circuit is provided for operating a smoke evacuator system for laser surgery and for indicating whether the filter used with the system is clogged.

BACKGROUND OF THE INVENTION

Related Applications

The present application relates to an electronic control circuit for a laser surgery smoke evacuator system. Two other applications are being filed simultaneously and are assigned to the assignee of the present application: the first relates to the smoke evacuator system as a whole Ser. No. 774,692, filed Sept. 11, 1985 entitled "Smoke Evacuators System For Use In Laser Surgery"; and, the second relates to a filter used with the system Ser. No. 774,690, filed Sept. 11, 1985 entitled "Filter Housing".

Laser surgery is becoming more common as surgical modality with a large variety of uses. When a tissue is subjected to a high energy laser beam the tissue is vaporized. It is desirable to remove the vapor and other by-products from the surgical site in a controlled manner. Smoke is intended to mean by-products of laser surgery which are primarily gases but can include some small amounts of liquid and solid particulate matter. The most common means of removing the vapor and other by-products is to use a suction tube at the surgical site to establish a flow of air which is then delivered to a filter placed in a housing with the motors and pumps that establish the vacuum flow.

Prior art smoke evacuator system, work adequately but are usually cumbersome, noisy and expensive. Many of these prior art systems have electronic circuits to indicate the clogged condition of the filter used with the system and these systems generally rely on determining a pressure differential across the filter or a flow rate through the filter. Such systems are often expensive and inaccurate.

It would be desirable to have an electronic circuit for a smoke evacuation system for laser surgery which would alleviate these problems.

SUMMARY OF THE INVENTION

The present invention provides an electronic circuit for running a vacuum pump and its associated motor at a variety of constant speeds in a thermally and acoustically insulated space.

The circuit includes an AC motor mounted inside the support casing for the smoke evacuator system. An air intake through the casing draws cooling air into the casing to cool the motor. A DC power supply is mounted inside the casing. An AC phase controller controls the motor speed. Because the motor and the phase controller dissipate a lot of heat particularly at low motor speeds, the phase controller is mounted near the air intake. The phase controller is shielded from electromotive interference.

The system also includes a vacuum pump, run by the motor and a filter mounted in an air inlet duct in fluid communications with the vacuum pump inlet. A filter clog circuit is powered by the DC power supply and generates a signal indicative of a clogged filter condition. A temperature sensor mounted in the air flow between the filter and the vacuum pump generates a signal indicative of the air flow and transmits this temperature signal to the filter clog circuit. A reference signal is also transmitted to the filter clog circuit. The filter clog circuit generates a trigger signal when the temperature signal exceeds the reference signal. A time delay circuit disables the clog circuit for a prescribed period of time after the motor is turned on so that initial transient heat buildup will not generate a false filter clog alarm. A gate is used to pass the trigger signal to a switch which turns on a light indicating that the filter is clogged.

The present electronic circuit provides a system which performs reliably at a variety of constant speed and dissipates the heat generated by the motor and the electronic components by using careful inter-relationship of the airflow and electronic components within the casing are also substantially surrounded by acoustical dampening material to reduce noise and this creates a further heat dissipation problem for the electrical circuitry. It is particularly important to properly dissipate heat generated inside the small casing for the system because the filter clog circuit uses temperature measurements to sense the clogged condition of the filter.

These and other features of the present invention will become apparent from the following detailed description of the preferred embodiments taken in conjunction with the following drawings:

DESCRIPTION OF THE DRAWINGS

FIG. 4 shows a detail circuit diagram of the filter clog circuit.

DETAILED DESCRIPTION OF THE PREFERRED EMBODIMENT

Figure 1:
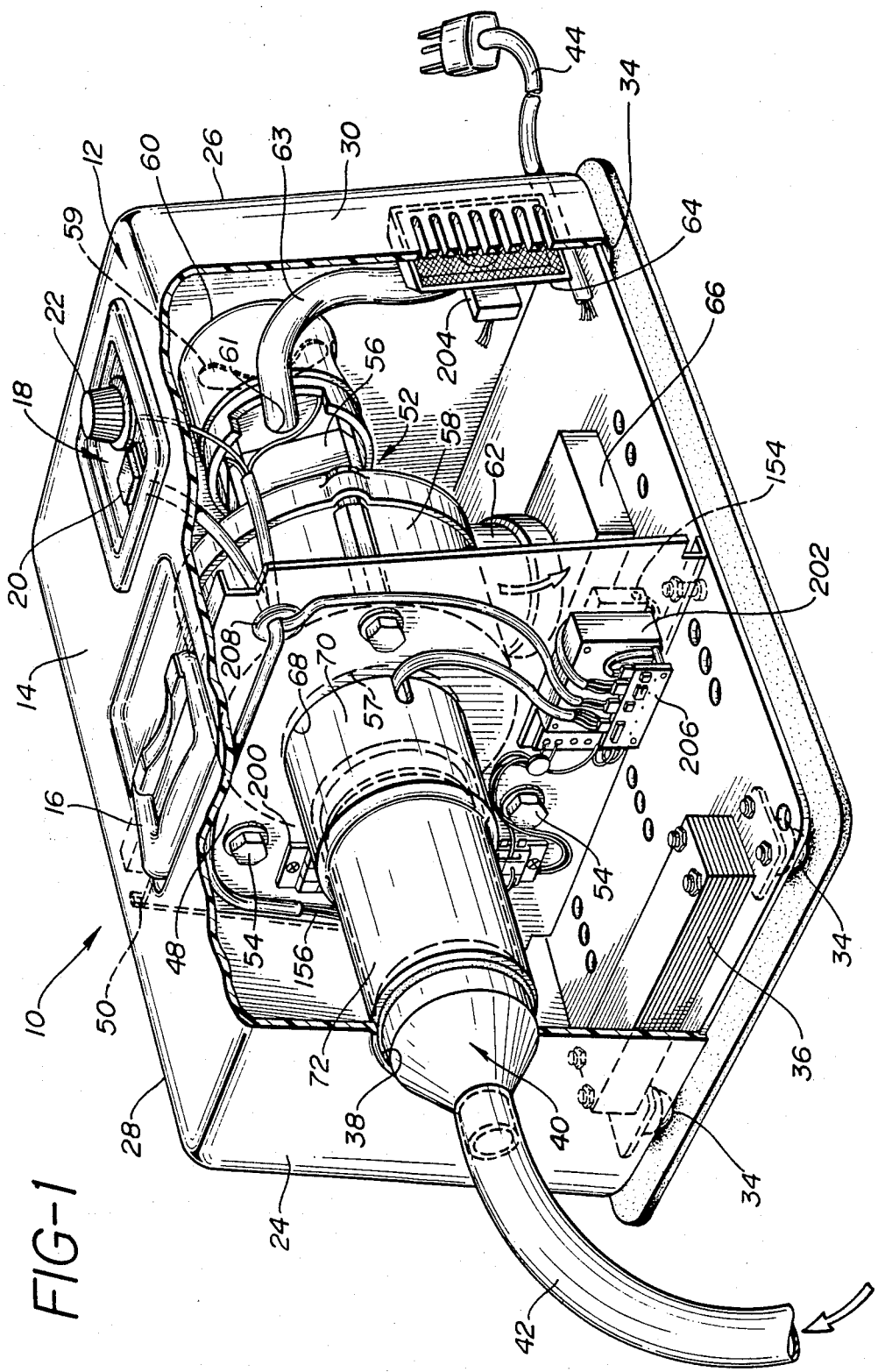
FIG. 1 shows a perspective view of the casing for the smoke evacuator partially broken away to show the location of the electrical elements inside the casing.

Referring now to FIG. 1 there is shown the laser surgery smoke evacuator system of the present invention.

The evacuator system 10 of the present invention is housed in a casing 12 having a top surface 14 on which a handle 16 and a control panel 18 are mounted. Control panel 18 has a warning light 20 to indicate a clogged filter condition and a control knob 22 for controlling the amount of suction provided by the apparatus. Casing 12 also includes a front surface 24, back surface 26 and sides 28 and 30. In the preferred embodiment, top 14, front 24, back 26 and sides 28 and 30 are all integrally formed of a high strength light-weight plastic material. A separate bottom panel 32 is removably affixed to casing 12 to provide an enclosure within casing 12. Wheels 34 are supported on bottom panel 32 for portability, and counterweights 36 are used to balance the unit.

Front surface 24 has a circular opening 38 therein through which filter 40 may be inserted into case 12. A suction tube 42 connects to filter 40 and has a convenient length for extending to the surgical site. An electrical power cord 44 provides power to the internal components of the system.

The interior of casing 12 is filled with sections of acoustical insulation (not shown) to reduce noise generated by the apparatus. These are various openings in the casing and the bottom panel for air vents and access openings for the components inside casing 12 which will be discussed later in the application.

Still referring to FIG. 1 there are shown certain interior components of the system. A mounting plate 48 fits in grooves 50 on the interior of top 14 and sides 28 and 30. A centrifugal vacuum pump 52 is mounted by means of bolts 54 to mounting plate 48.

Vacuum pump 52 includes an alternating current and voltage vacuum motor 56, an impeller chamber 58, an exhaust horn and optional exhaust muffler 66 mounted on bottom panel 32 to reduce exhaust noise. Impeller blades (not shown) are mounted on the shaft (not shown) of motor 56 and rotate within impeller chamber 58 to create a negative pressure in chamber 58.

A filter collar 70 and filter duct 72, which are disposed on the opposite side of mounting plate 48 from motor 56 inter-aligned generally coaxially with the motor. Filter duct 72 fits flush with opening 38 in the front wall 24 of casing 12 and receives filter 40. It is preferred that filter duct 72 be bonded to the peripheral surface of opening 38 to reduce vibration.

The inlet 57 to impeller chamber 58 is a generally circular opening aligned coaxially with a circular opening 68 in mounting plate 48. Exhaust horn 62 from impeller chamber 58 extends tangentially from generally cylindrical impeller chamber 58 so that the airflow exits impeller chamber 58 without impinging upon the electrical windings of motor 56. As an alternative feature an exhaust pipe may be connected to exhaust horn 62 and exit through an appropriate opening in casing 12 to connect with the normal exhaust in the operating room.

A cooling fan 59 is mounted in the vicinity of the electrical windings of motor 56 and covered by a liquid sealed cap 60 having an intake port 61 which connects to an intake pipe 63 which in turn connects to an intake manifold 64 mounted on the inside of casing 12 in the vicinity of intake vents conveniently located through casing 12.

Figure 2:
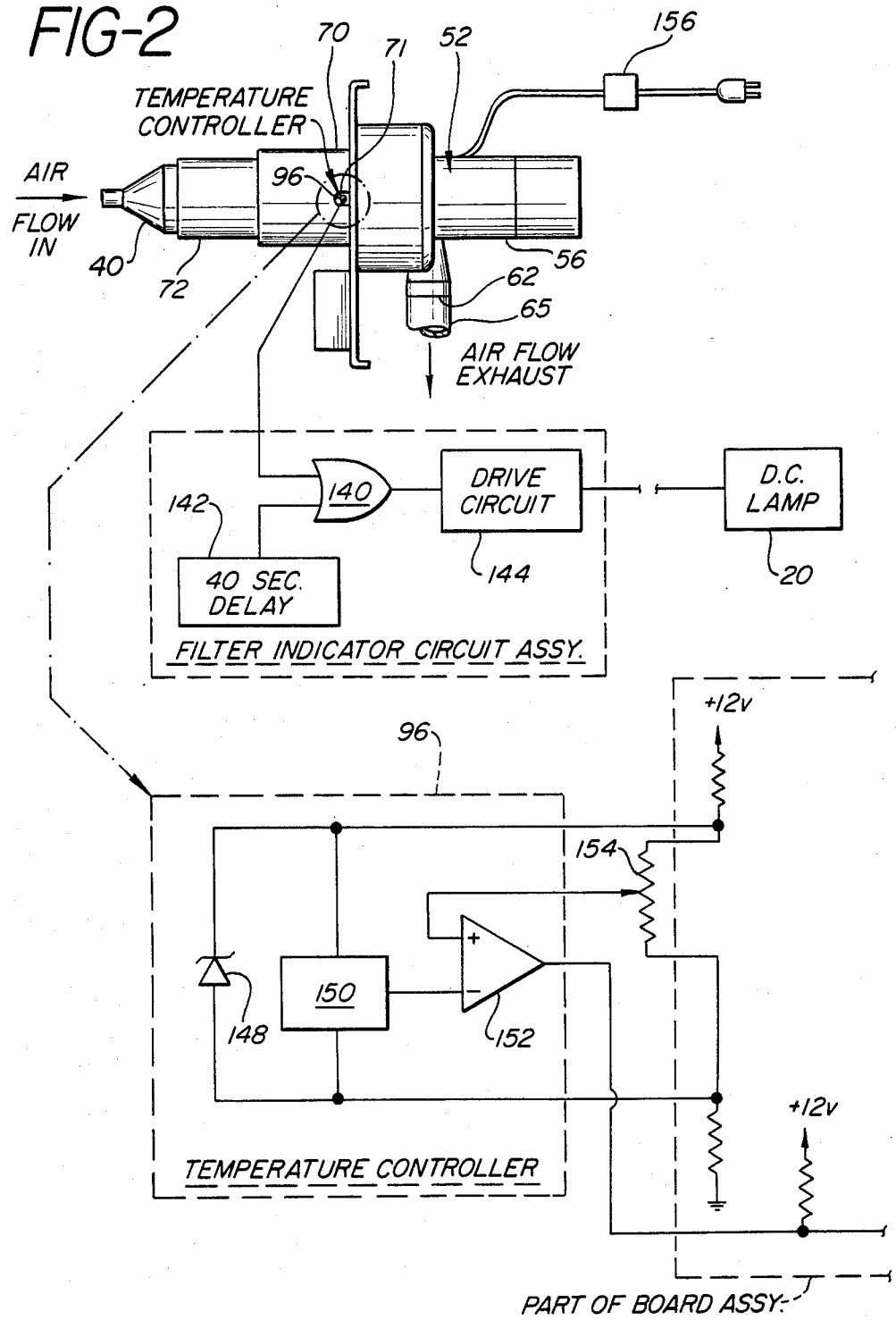
FIG. 2 shows a schematic block diagram of the circuit for determining the clogged condition of the filter.

As seen in FIG. 2, a temperature controller circuit 96 is mounted through slot 71 in the filter collar 70. Temperature controller circuit 96 monitors the temperature downstream of filter 40 and upstream of impeller chamber 58. A variety of devices can be used as temperature sensors including thermocouples or thermisters or other suitable temperature sensors well-known in the art. Temperature controller circuit 96 is connected to suitable electronic circuitry disposed within casing 12 for generating a signal to activate a warning light or bell when filter 40 becomes clogged. This electronic circuitry will be discussed in general in connection with the block diagram shown in FIG. 2 and more particularly in connection with FIGS. 3 and 4.

Referring to FIG. 1 there are shown various electronic components assembled onto mounting plate 48.

Thermostat 156 is used to turn off the power to the vacuum pump 52 if a clogged condition exists in the filter long enough to cause the system to overheat. A 15 amp 160° F. + or (−)5° F. thermostat was chosen. It was found that the thermostat temperature runs approximately 20° F. lower than the temperature of the motor which would indicate a low cutoff temperature of 175° F. for the motor and a high cutoff temperature for about 185° F. for the motor. We have found that this overheat condition only occurs if the unit runs with a very dirty filter for extended period of time typically over thirty minutes. It is hoped that the user would notice the alarm indicator well within this time and change the filter before the thermostat was tripped. The thermostat resets when temperature cools down to approximately 20° F. below trip point.

Terminal board 200 is mounted on mounting plate 48 with 8 rows of 4 columns each.

Power supply 202 is a 12 volt DC power supply that feeds the overall electronic system. AC phase controller 204 is mounted in a cool place as will be explained later in the application next to intake manifold 64 on the inside of the cabinet particularly on wall 30. At low speeds the power dissipated across phase controller 204 can produce heat and voltage fluctuations which would prevent motor 56 from operating in a constant speed. This problem has been solved by placing phase controller 204 in a cool place next to the intake manifold 64 for cooling motor 56.

Temperature controller circuit 96 is mounted in the chamber within collar 20 downstream of filter 40. The printed circuit board 206 for the filter clog condition indicator circuit is mounted on power supply 202. Jack and pin connectors J1, J2, J3, J4 and P1, P2, P3, and P4 are mounted on printed circuit board 206.

Suitable wiring harnasses and pin connectors are provided for connecting the circuit together. Access hole and grommet 208 are mounted on mounting plate 48 to permit wires to pass from one side of mounting plate 48 to the other.

A trip adjustment potentiometer 154 is also mounted on mounting plate 48 near the bottom of the casing and aligned with an access hole so that potentiometer 154 can be adjusted to calibrate the instrument.

Referring now to FIG. 2 a schematic block diagram of the electronic circuit for the filter clog indicator will be described Temperature controller circuit 96 generates a signal indicative of the air flow temperature having exceeded for not a limit and transmits that signal to an OR gate 140. A temperature delay circuit 142 has a built in nominal forty second delay to cause the circuit to ignore temperature readings for a forty seconds lapse of time every time one turns the unit on. This eliminates false indications due to internal temperature increases immediately after the system is turned on. If the signal delivered to the OR gate 140 by either temperature controller circuit 96 or time delay circuit 142 is high then the output of OR gate 140 remains high and keeps drive circuit 144 turned off and correspondingly the warning device (which in the preferred embodiment is a light 20 but may also be an audible alarm) is kept off. If both of the signals delivered to the OR gate 140 by temperature controller circuit 96 and time delay circuit 142 are low, the output of OR gate 140 will go low and turn on drive circuit 144 and turn on light 20.

The time delay circuit is typically a type 555 integrated circuit monostable multi-vibrator in which the resistance capacitive levels are chosen to set the desired time constant.

The temperature controller circuit 96 is shown also in FIG. 2 and includes a Zener diode 148, a sensor, preferably a thermocouple 150, and a comparator 152. Circuit 96 is typically a type LM-3911 temperature controller circuit where reference voltage is provided by the Zener diode 148 and a trip voltage is set on the potentiometer 154 so that when the output of thermocouple 150 reaches the calibrated trip volage the output of temperature controller circuit 96 goes low. If time delay circuit 142 is also low, the output of OR gate 140 will go low and turn on lamp 20 through drive circuit 144.

Referring to FIGS. 1 and 2 the thermostat 156 is mounted on mounting plate 48 and connected between the source of electrical power and vacuum motor 56 to turn off the power and thus vacuum motor 56 in response to an overheat condition. Thermostat 156 is mounted on mounting plate 48 because that is one of the warmer spots within casing 12. Thermostat 156 shuts of the power if a clogged filter condition exists for an extended period of time.

Figure 3:
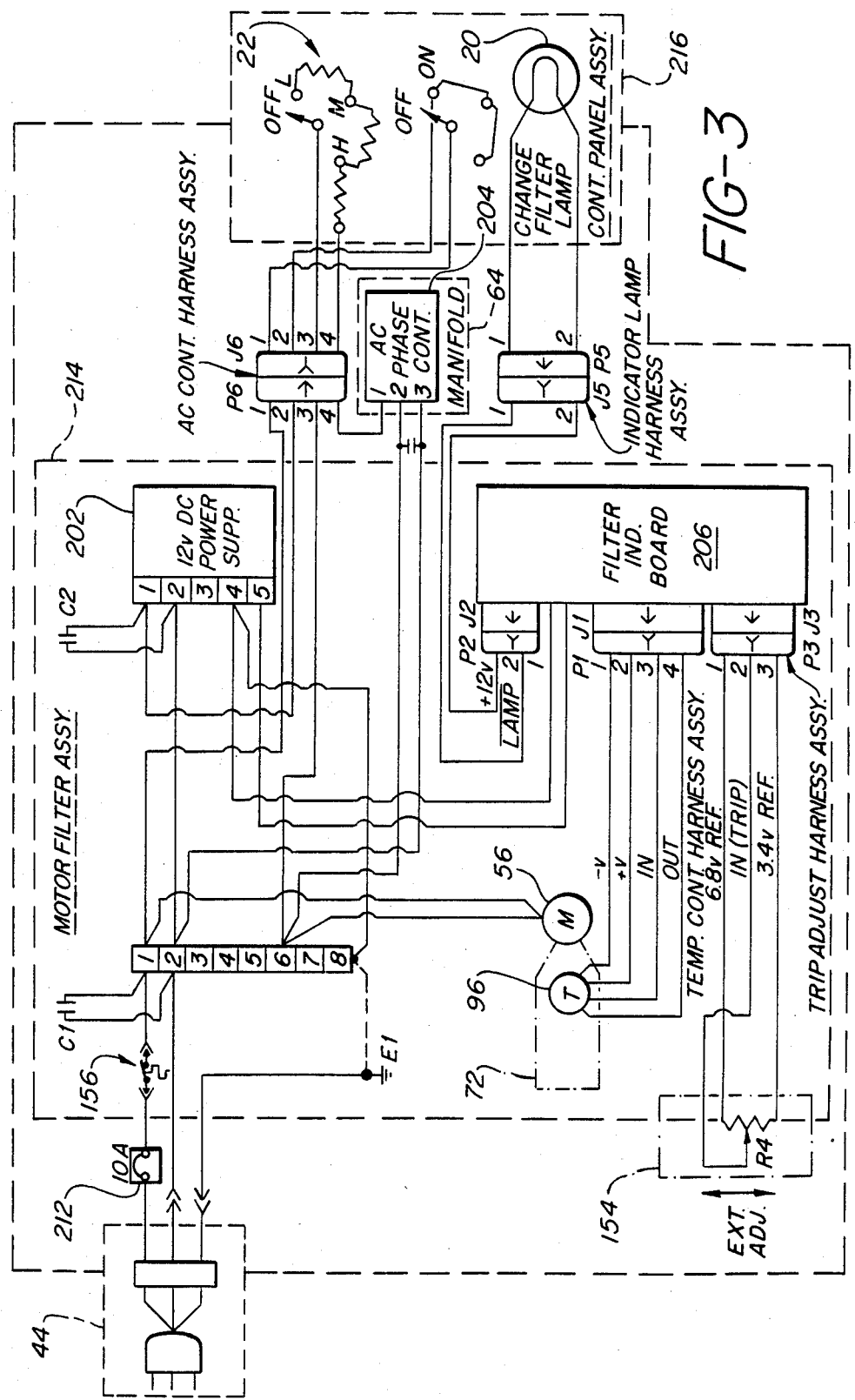
FIG. 3 shows an overall circuit for the system.

The overall circuit of the present invention is shown in FIG. 3 where there is shown a grounded power cord 44, a circuit breaker 212, a motor filter assembly 214, a control panel 216 on which control switch 22 is mounted. Control switch 22 is shown as a double pole multi-position switch. Alternatively, it could be infinitely variable switch between two limits. Lamp 20 is also shown on control panel 216. Phase control circuit 204 is shown mounted in the vicinity of intake manifold 64.

Motor filter assembly 214 includes motor 56, filter duct 72, and temperature controller circuit 96 which in this case is a LM 3911 chip. Trip adjustment potentiometer 154 is shown as having access to the exterior of case 12. Filter assembly printed circuit 206 is shown schematically in FIG. 3 and in more detail in FIG. 4.

In FIG. 3 temperature controller circuit 96 is shown connected through a pin $P_1$ and jack $J_1$ connector to board 206. Lamp 20 is shown connected to board 206 through pin $P_2$ and jack $J_2$, trip adjuster potentiometer 154 is shown connected to printed circuit board 206 through pin $P_3$ and jack $J_3$.

An added feature of test points can be added to printed circuit board 206 and brought out through quick connect receptacles to conduct test on the system to be used principally during assembly of the circuit. These are not shown in the present invention.

FIG. 4. shows the detail circuit diagram for the printed circuit board for the filter clog circuit. Connector J1 for temperature controller circuit 96 is connected through its pin 1 to ground and its pin 2 to power supply 202 through a limiting resistor $R_4$. The output of temperature controller circuit 96 is connected through pin 4 of J1 directly to one input of OR gate U2. The input of temperature controller circuit 96 is connected through pin 3 of J1 to trip adjustment potentiometer 154 and to the power supply of pin 2 with an intervening smoothing capacitor C4. Delay circuit U1 is a type 555 integrated circuit monostable multi vibrator. The resistance and capacitive values of R1, R2, R3, and C2 are chosen to provide the desired time constant for delay circuit U1. The output of delay circuit U1 is delivered over its pin 3 to pin 1 of OR gate U2.

The logic of OR gate U2 provides that if the signal from temperature controller circuit 96 is low at the same time the signal from delay circuit U1 is low then the output at pin 3 of U2 will go low and turn on transistor Q1 to complete the circuit and light lamp 20 to indicate an alarm condition that the filter is clogged. If the signal on pin 1 of OR gate U2 is high indicating a low temperature then the output of OR gate U2 will be high and transistor Q1 will not turn on. If the output from delay circuit U1 is high, then a high signal will appear at pin 1 of OR gate U2 and output at pin 3 of OR gate U2 will remain high and transistor Q1 will not turn on. Delay circuit U2 provides a high output for a specified time after the circuit is turned on to eliminate an alarm condition during the transient startup period for the system.

Capacitors C5 and C6 are used to decouple U1 and U2 at the power supply and ground connection of those components. Resistor R4 is used as a limiting resistor for Zener diode 148 through pin 1 of connector J3. This reference voltage is also used for trip adjustment potentiometer 154. Resistor R6 is similarly used for providing a divided down reference voltage on pin 3 of connector J3 of potentiometer 154.

Returning again to FIG. 3 there is shown a filter capacitor across pins 2 and 3 of phase controller 204. The purpose of this capacitor is to eliminate electromagnetic interference from motor 56.

The present invention has been described in conjunction with certain preferred embodiments. Those skilled in the art will appreciate that many modification and changes may be made to the preferred embodiments without departing from the spirit of the present invention. It is therefore, not intended to limit the present invention except to set forth in the appended claims.

What is claimed is:

1. A smoke evacuator system comprising:

a motor operative in response to alternating current supplied thereto;

a vacuum pump run by said motor;

a duct in fluid communication with said vacuum pump such that air and smoke are drawn through said duct by said pump;

a filter mounted in said duct;

a direct current power supply operative in response to said alternating current supplied to said motor;

a filter clogged indicating circuit powered by said direct current power supply for generating a signal indicative of the clogged condition of said filter and including:

a temperature controller circuit disposed in the air flow between said filter and said vacuum pump for generating a signal indicative of the temperature of said air flow and transmitting said temperature signal to said filter clog circuit;

means for setting a temperature reference signal in said filter clog circuit and including a potentiometer;

means for generating a trigger signal when said temperature indicating signal exceeds said reference signal;

time delay circuit means in said filter clog circuit for generating a time delay signal for a prescribed time period after said circuit is initially energized;

gate means in said filter clog circuit for receiving said trigger signal and said time delay signal, said gate means operative to transmit said trigger signal only after said prescribed time delay has passed; and, indicator means operative in response to said trigger signal transmitted by said gate means for indicating that said filter is clogged.

2. The system of claim 1 further including capacitor filter means in said filter clog circuit operative to decouple said time delay circuit means from said gate means.

3. The system of claim 1 wherein said time delay circuit means includes a type 555 integrated circuit monostable multi vibrator.

* * * * *